US007725818B1

(12) United States Patent
Krishnan et al.

(10) Patent No.: US 7,725,818 B1
(45) Date of Patent: May 25, 2010

(54) PARALLEL COMPOSITION OF ELECTRONIC RESPONSES TO ELECTRONIC REQUESTS

(75) Inventors: Gopal Krishnan, Austin, TX (US);
Chaitanya Laxminarayan, Austin, TX (US)

(73) Assignee: International Business Machines Corporation, Armonk, NY (US)

( * ) Notice: Subject to any disclaimer, the term of this patent is extended or adjusted under 35 U.S.C. 154(b) by 1202 days.

(21) Appl. No.: 11/297,007

(22) Filed: Dec. 8, 2005

Related U.S. Application Data

(60) Provisional application No. 60/642,165, filed on Jan. 6, 2005.

(51) Int. Cl.
*G06F 17/00* (2006.01)
(52) U.S. Cl. .......................... 715/237; 715/234; 705/2; 705/3; 705/4
(58) Field of Classification Search .................. 715/237, 715/224; 705/4
See application file for complete search history.

(56) References Cited

U.S. PATENT DOCUMENTS

| | | | |
|---|---|---|---|
| 5,758,126 A * | 5/1998 | Daniels et al. ............. 715/780 |
| 5,991,731 A * | 11/1999 | Colon et al. ................ 705/3 |
| 6,185,583 B1 * | 2/2001 | Blando ........................ 715/210 |
| 6,516,353 B1 * | 2/2003 | Richards .................... 719/310 |
| 7,251,782 B1 * | 7/2007 | Albers et al. ............... 715/711 |
| 2004/0193512 A1 * | 9/2004 | Gobin et al. ................ 705/29 |
| 2004/0226002 A1 * | 11/2004 | Larcheveque et al. ...... 717/126 |
| 2004/0261017 A1 * | 12/2004 | Perry .......................... 715/513 |
| 2004/0268229 A1 * | 12/2004 | Paoli et al. ................. 715/508 |
| 2005/0114712 A1 * | 5/2005 | Devine et al. .............. 713/201 |
| 2005/0144278 A1 * | 6/2005 | Atamaniouk ............... 709/225 |
| 2005/0216421 A1 * | 9/2005 | Barry et al. ................ 705/64 |
| 2005/0251429 A1 * | 11/2005 | Ammer et al. ............. 705/4 |
| 2007/0050219 A1 * | 3/2007 | Sohr et al. .................. 705/4 |
| 2007/0198432 A1 * | 8/2007 | Pitroda et al. .............. 705/64 |
| 2007/0203753 A1 * | 8/2007 | Hasan et al. ................ 705/3 |
| 2008/0114657 A1 * | 5/2008 | Forzley ...................... 705/14 |

OTHER PUBLICATIONS

Title: XML-Based Claims Attachments Techincal Tutorial Date: Aug. 28, 2003 Author: W. Rishel Url [retrieved Aug. 28, 2009]: <http://www.bus.umich.edu/KresgePublic/Journals/Gartner/research/117000/117034/117034.pdf>.*

(Continued)

*Primary Examiner*—Doug Hutton
*Assistant Examiner*—Mustafa Amin
(74) *Attorney, Agent, or Firm*—Stevens & Showalter LLP

(57) ABSTRACT

A method for automatic parallel processing of the steps involved in composing electronic responses to structured electronic requests where the request and the response contain some common fields of information. The process starts subsequent processing steps before the validation of the request is complete. A structurally complete, but partial response to a request is prepared as soon as it is possible to construct that response structure. The response structure is determined from personalization factors for the requestor, and a response template is created. The personalized response document is a skeleton created with known data from the minimum validation of the request, and with placeholders for data that has not yet been determined. The response is selectively populated with data from the request when the format of the response is determined. As additional information becomes available during the processing of the request, that additional data is placed into the response structure.

20 Claims, 7 Drawing Sheets

OTHER PUBLICATIONS

Title: Posting File Partitioning and Parallel information Reterieval Journal: The Journal of Systems and Software vol. 63, issue 2, Aug. 15, 2002 Authors: Yung-Cheng Ma, Tien-Fu Chen, Chung-Ping Chung.*

Title: HIPAA and Claims Attachments Preparing for Regulation Date: May 2004 url [retrieved on Aug. 28, 2009]: <http://staging.hl7.org/participate/Documents/HIPAA_and_Claims_Attachments_White_Paper_20040518.pdf>.*

Title: HIPAA Transaxtion standard & Electronic Data Interchange Date: Feb. 26, 2004; Url <http://docs.google.com/gview?a=v&q=cache:HjNultGe-ycJ:https://providerinfosource.healthlink.com/wps/wcm/connect/resources/file/eb73b44388302ba/hipaa_edi_guide.pdf%3FMOD%3DAJPERES+%22hipaa+transaction+standard+%26+electronic+data+interchange%22&hl=en&gl=us>.*

* cited by examiner

PARALLEL COMPOSITION OF ELECTRONIC RESPONSES TO ELECTRONIC REQUESTS

CROSS-REFERENCE TO RELATED APPLICATIONS

This application claims the benefit of PPA Ser. No. 60/642,165, filed Jan. 6, 2005 by the present inventors.

FIELD OF THE INVENTION

This innovation relates to computer applications, and, more particularly, to automated methods for the composition of electronic responses to electronic requests.

BACKGROUND OF THE INVENTION

For speed of communications and cost effectiveness, individuals, businesses, and other organizations frequently exchange electronic data through e-mail, the Internet, and other networks and systems. Often this data comprises electronic requests for information from businesses. To compete effectively in the marketplace, businesses that must compose electronic responses to such electronic requests must process a large number of these transactions quickly.

For example, insurance companies may receive electronic requests comprising documents in compliance with the following standards:
  HIPAA (Health Insurance Portability and Accountability Act)—for requests about health insurance coverage for a patient's treatment by a health provider; and
  ACORD (Association for Cooperative Operations Research and Development)—for requests about automobile and personal insurance coverage for a client.

Typically, insurance companies or their representatives use software applications to process these requests automatically, completing each step independently in a required linear sequence, and then compose electronic responses to these requests and send the responses to the requesting parties.

Example of a HIPAA Request and Response

For example, in the health insurance industry, a health care provider, such as a doctor's office or hospital, may send an electronic request for insurance coverage, for a patient who needs treatment, to an insurance company. The request may be an ANSI (American National Standards Institute) 270 document in compliance with HIPAA standards. The insurance company receives the request over a network such as the Internet and then employs an application to process the request to determine the patient's eligibility for coverage and the patient's exact benefits before sending an ANSI 271 response to the health care provider. As shown in FIG. 1, before a response can be sent this processing requires a number of actions to be performed in a set sequence, such as the following:

Validating the request 610.
  The application determines whether the request is a readable ANSI 270 document that is in the correct format and contains meaningful data.
Decomposing the information in the request 620.
  The processing application obtains the data contained in the request from the appropriate fields.
Fetching response data 630.
  The application uses the data obtained from the request to determine the patient's eligibility for the treatment and the patient's exact benefits coverage.
Composing the response 640.
  The application composes an ANSI 271 response to the request, containing the appropriate information.
Validating the response 650.
  The application determines that the response that has been assembled is a readable ANSI 271 document that is in the correct format and contains meaningful data.

Linear processing of electronic requests, such as in the example given above, may proceed quickly enough to be satisfactory for an individual transaction. But businesses often must process many thousands of requests in short time periods, so that the processing time for such transactions adds up substantially and can cause delays unacceptable to customers and employees. For example, some businesses process 102 or more requests per second, amounting to 367,200 requests per hour. Moreover, delays because of errors located at any step in the process may cause significant bottlenecks that further reduce productivity and increase business costs.

To compensate for such problems with processing requests, businesses often employ larger and more capable computers or combinations of linked computers to decrease processing time, which are expensive solutions.

Therefore, there is a need for a system and method for automatically composing electronic responses to electronic requests that decreases processing time and reduces potential bottlenecks.

BRIEF SUMMARY OF THE INVENTION

These and other needs are addressed by the present invention. The following explanation describes the present invention by way of example and not by way of limitation.

It is an object of the present invention to provide automatic parallel processing for the composition of electronic responses to electronic requests. In the current invention, the term parallel processing refers to the concurrent execution of tasks. Typically, the tasks are executed on a single computer, but they may be distributed for execution on two or more computers.

Some electronic processing guidelines, such as insurance requests, require a complete validation of the format or other features of the request. In the vast majority of these cases, perhaps over 99% of the time, this validation will be satisfied.

One aspect of the current invention is that it starts subsequent processing steps before the validation is complete. This aspect is called parallel processing request responses. If the validation fails, then all tasks are abandoned and additional information is requested. However, if the validation is successful, then the overall completion time of the processing is reduced. An analogous practice in computer architecture is branch prediction where the two outcomes for an IF statement are pursued in parallel until the condition is determined and one path is stopped. The branch prediction eliminates stall cycles waiting for the condition to be determined. The present invention is typically more efficient than branch prediction because in most cases the request will be validated, and there is little computation lost in those cases where validation ultimately fails.

Another aspect of the current invention is that it prepares a structurally complete, but partial response to a request as soon as it is able to construct that response structure. The commencement of preparing a response before completing the entire validation is called minimum validation of the request. For instance, for insurance requests, HIPAA regulations require a complete validation of all fields in the request, but from a practical perspective only a few of these fields are important to the request. Once those few fields have been validated, processing of the request can continue in parallel with the validation of the remaining fields in the request.

Typically the response structure is determined from personalization factors for the requestor. Personalization factors are described in more detail in copending application Ser. No. 11/123,630 filed Apr. 30, 2005. In one embodiment of the current invention, the identity of the requestor is determined at the time that the request is received, the personalization factors are determined for the requestor, and the format of the response is established. This aspect is called predetermining the response document. The personalized response document is a skeleton created with known data from the minimum validation of the request, and with placeholders for data that has not yet been determined. This approach is contrasted with the prior art practice of creating a data string and validating entirely after the composition of the response.

Another aspect of the current invention is that some data in the request is typically included in the response. As soon as the format of the response is determined from the personalization factors, this common data is added into the response. This aspect is called selectively populating request responses. The personalization factors are typically created from known trading partner profiles for entities which are expected to make a request. Response templates may be created for these profiles, either created upon the request or recalled from memory or storage. As additional information becomes available during the processing of the request, that additional data is placed into the response structure.

In accordance with the present invention, a method is provided for automatic parallel processing of the steps involved in composing electronic responses to structured electronic requests where the request and the response contain some common fields of information. The process starts subsequent processing steps before the validation of the request is complete. A structurally complete, but partial response to a request is prepared as soon as it is possible to construct that response structure. The response structure is determined from personalization factors for the requestor, and a response template is created. The personalized response document is a skeleton created with known data from the minimum validation of the request, and with placeholders for data that has not yet been determined. The response is selectively populated with data from the request when the format of the response is determined. As additional information becomes available during the processing of the request, that additional data is placed into the response structure.

BRIEF DESCRIPTION OF THE DRAWINGS

The following embodiment of the present invention is described by way of example only, with reference to the accompanying drawings, in which.

DETAILED DESCRIPTION

The following description explains a system and method in accordance with the present invention. The details of this explanation are offered to illustrate the present invention clearly. However, it will be apparent to those skilled in the art that the concepts of the present invention are not limited to these specific details. Commonly known elements are also shown in block diagrams for clarity, as examples and not as limitations of the present invention.

Operating Environment

Figure 1:
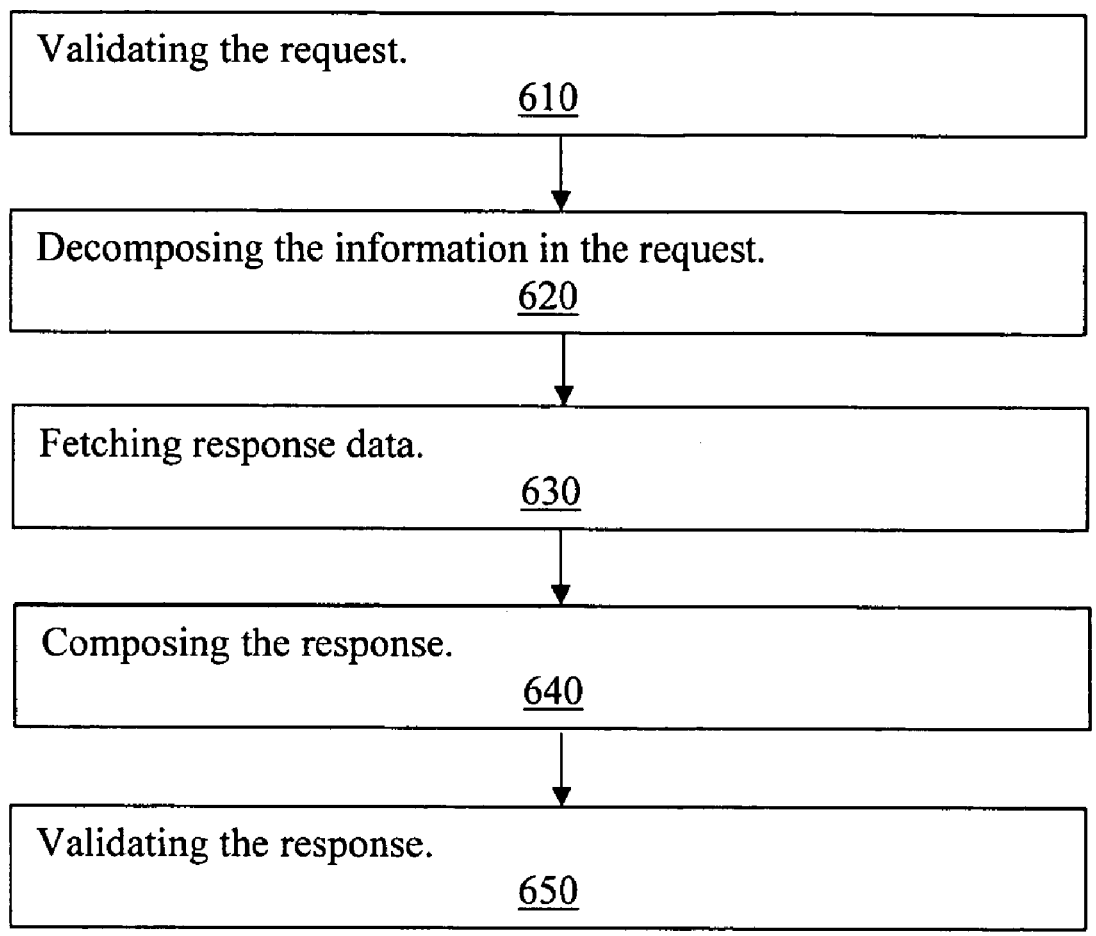
FIG. 1 is a flow chart that illustrates at a high level a linear process for automatically composing an electronic response to an electronic request.
Figure 2:
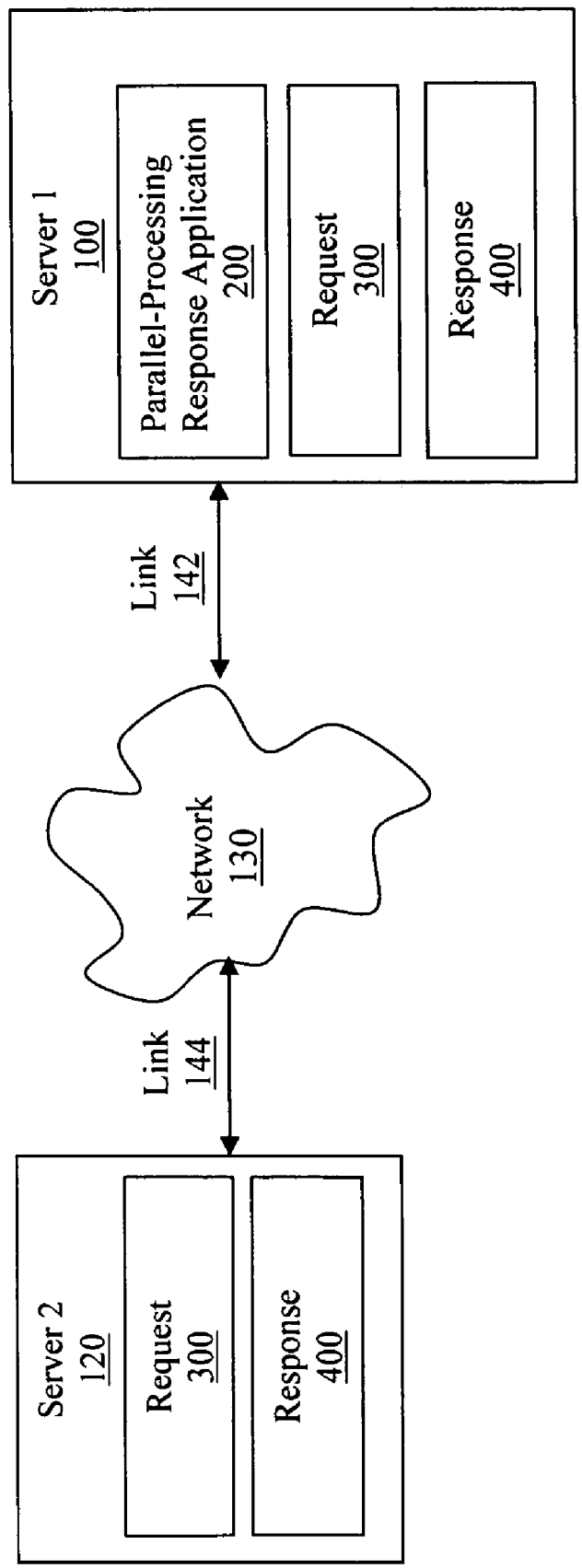
FIG. 2 is a block diagram showing an operating environment in which embodiments of the present invention may be employed.

An embodiment of the operating environment of the present invention is shown in FIG. 2. One or more programmers at server 1 100 create a parallel-processing response application 200 that uses the method of the present invention explained below.

Server 1 100 and server 2 120 can communicate via wired or wireless links 142 and 144 and a wired or wireless network 130. The servers 1 100 and 2 120 may be personal computers or larger computerized systems or combinations of systems. The network 130 may be the Internet, a private LAN (Local Area Network), a wireless network, a TCP/IP (Transmission Control Protocol/Internet Protocol) network, or other communications system, and can comprise multiple elements such as gateways, routers, and switches. Links 142 and 144 use technology appropriate for communications with network 130.

Thus, a party or application at server 2 120 can send an electronic request 300 to server 1 100. Server 1 100 can then use the parallel-processing response application 200 to automatically process the request 300, using the method of the present invention explained below. The parallel-processing response application 200 then composes an electronic response 400 and sends the response 400 to server 2 120.

In other embodiments, after the creation of the parallel-processing response application 200 on one server, the parallel-processing response application 200 can be transferred to other servers or computing environments for use there.

In still other embodiments, elements of the system given above may also be used on one or more different servers, or other computing environments.

Process

Figure 3:
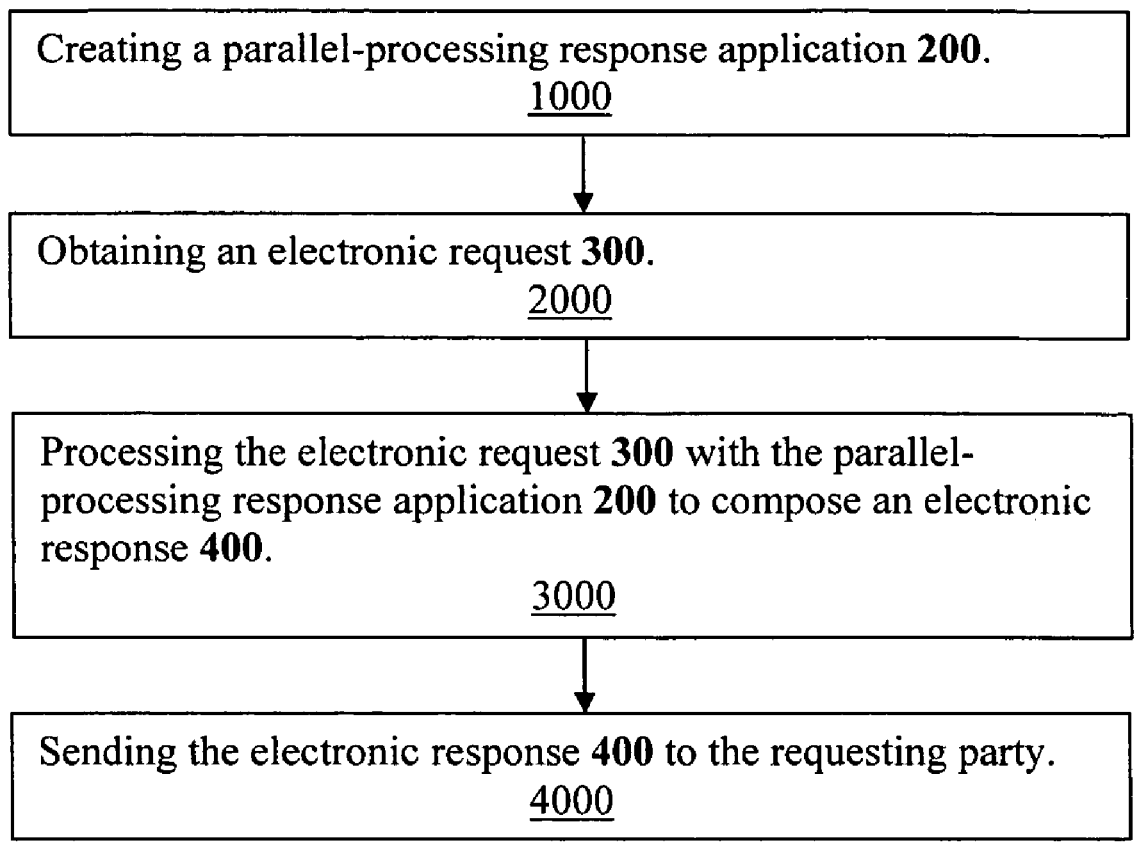
FIG. 3 is a flow chart that illustrates at a high level a process for using a parallel-processing response application to automatically compose an electronic response to an electronic request.

FIG. 3 is a flow chart that illustrates a process for employing parallel processing for the composition of electronic responses to electronic requests in an embodiment. It will be useful to explain these elements briefly from a high level and then to expand them in detail.

Step 1000 in FIG. 3—A party at a server 100 creates a parallel-processing response application 200.

Step 2000 in FIG. 3—The parallel-processing response application 200 obtains an electronic request 300 that requires an electronic response.

Step 3000 in FIG. 3—The parallel-processing response application 200 automatically processes the request 300 and composes an electronic response 400.

Step 4000 in FIG. 3—The parallel-processing response application 200 sends the electronic response 400 to the requesting party.

Creating a Parallel-Processing Response Application

As mentioned above, in an embodiment one or more programmers at server 1100, shown in FIG. 2, create the parallel-processing response application 200 for use there. In another embodiment, the parallel-processing response application 200 may be created on one server and loaded onto any other server or computing environment for use there.

Steps in the Process

Figure 4:
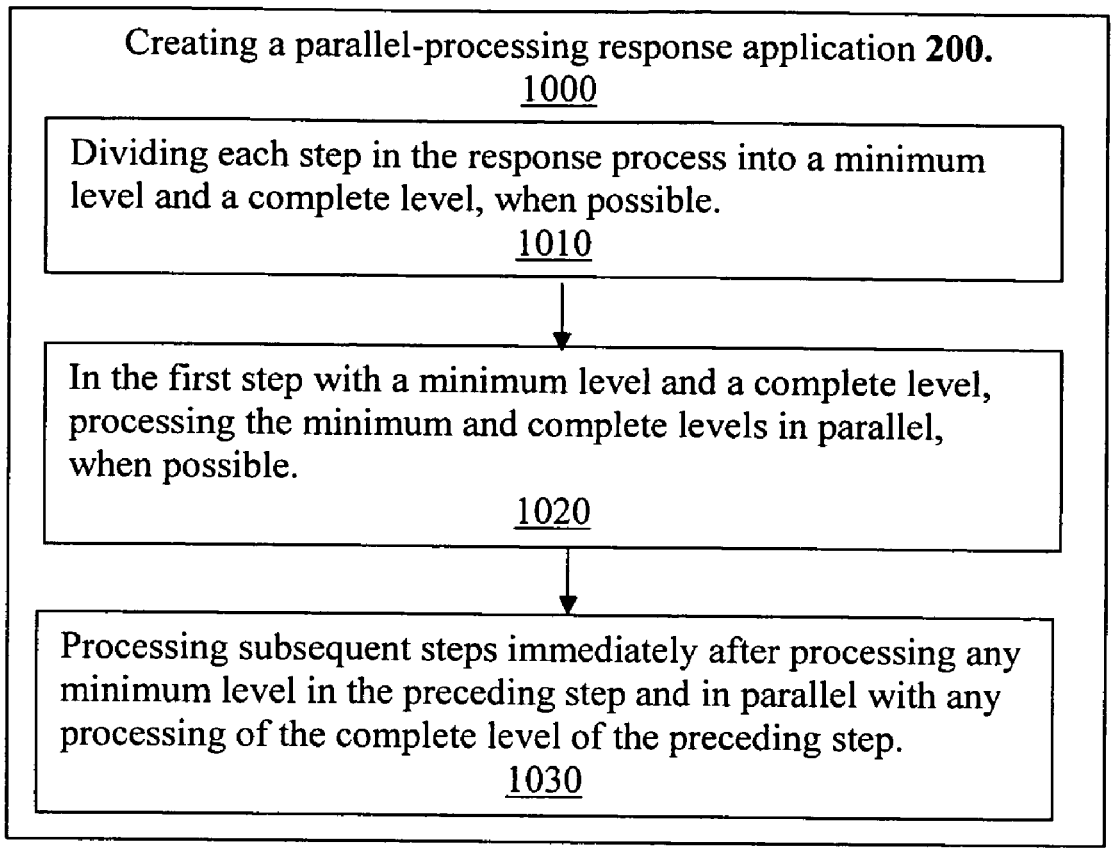
FIG. 4 is a flow chart that illustrates at a high level a process for creating a parallel-processing response application.

As shown in FIG. 4, a process for creating a parallel-processing response application 200, in an embodiment, is to design the application to accomplish the following steps:

Step 1010 in FIG. 4—Dividing each step in the response process into a minimum level and a complete level, when possible.

Step 1020 in FIG. 4—In the first step with a minimum level and a complete level, processing the minimum and complete levels in parallel, when possible.

Step 1030 in FIG. 4—Processing subsequent steps immediately after processing any minimum level in the preceding step and in parallel with any processing of the complete level of the preceding step.

Step 1010 in FIG. 4—Dividing each step in the response process into a minimum level and a complete level.

The present invention can be employed under two conditions:

1. The request and the response must contain some common fields of information; and
2. The process for validating the request must be segmentable into
   A minimal level, and
   A complete level.

The minimum and complete levels may be defined as is useful. For example, in an embodiment the minimal level may comprise validating the structure of the request, such as the required format. The complete level would then comprise processing the data in the request.

In another embodiment, the minimal level may comprise validating the structure of the request and also processing data from a specified set of fields in the request. The complete level would then comprise processing the data from the fields of the request not in the minimum level set.

Example of a HIPAA Request and Response Transaction

The following lines of code are an example of segments of a HIPAA request and response transaction, comprising An ANSI 270 request for patient eligibility and benefits coverage; and A corresponding ANSI 271 response.

In this example important fields that are common between the request and the response are underlined for clarity. The example also illustrates the structural format required for HIPAA for such a transaction.

ANSI 270 Request

ISA*00* *00* *ZZ*WEBIFYSE *ZZ*00123 *041210*1956*U*00401*000783397*0*P*:~

GS*HS*WEBIFYSE*058916206POC*20041210*1956*1*X*004010X092A1~

ST*270*112780~

BHT*0022*13*11836412*20041210*1956~

HL*1**20*1~

NM1*PR*2*<u>PAYERX</u>*****PI*<u>123456</u>~

HL*2*1*21*1~

NM1*1P*2*<u>PROVIDERY</u>*****FI*<u>333666999</u>~

HL*3*2*22*1~

NM1*IL*1*<u>DOE*JANE</u>****MI*<u>XXX123456789</u>~

HL*4*3*23*0~

TRN*1*1.183641.2*8877988*Y~

NM1*03*1*<u>DOE*JOHN</u>*~

N3*<u>1234SMALLLN</u>~

N4*<u>AUSTIN*TX*12345</u>~

DMG*D8*<u>19810911</u>*M~

DTP*472*D8*20041210~

EQ*30***GP~

SE*17*112780~

GE*1*1~

IEA*1*000783397~

ANSI 271 Response

ISA*00* *00* *ZZ*00123 *ZZ*WEBIFYSE *041210*1955*U*00401*000783397*0*P*:~

GS*HB*058916206POC*WEBIFYSE*20041210*1955580*1*X*004010X092A1~

ST*271*112780~

BHT*0022*11*11836412*20041210*19555800~

HL*1**20*1~

NM1*PR*2*<u>PAYERX</u>*****PI*<u>123456</u>~

HL*2*1*21*1~

NM1*1P*2*<u>PROVIDERY</u>*****FI*<u>333666999</u>~

HL*3*2*22*1~

NM1*IL*1*<u>DOE*JANE</u>****MI*<u>XXX123456789</u>~

HL*4*3*23*0~

TRN*2*1.183641.2*8877988~

NM1*03*1*<u>DOE*JOHN</u>****MI*XXX123456789~

N3*<u>1234SMALLLN</u>~

N4*<u>AUSTIN*TX*12345</u>~

DMG*D8*<u>19810911</u>*M~

INS*N*19~

EB*1***IN*PLAN XYZ~

DTP*636*D8*20041209~

DTP*307*RD8*20040701-99991231~

SE*19*112780~

GE*1*1~

IEA*1*000783397~

The underlined fields in the example above may be characterized in the following way:

| Field Name | Data in Example | Structural Format Required for Data |
|---|---|---|
| Payer Name | PAYER X | Alphanumeric 1-35 Characters |
| Payer ID | 123456 | Alphanumeric 2-80 Characters |

-continued

| Field Name | Data in Example | Structural Format Required for Data |
|---|---|---|
| Provider Name | PROVIDER Y | Alphanumeric 1-35 Characters |
| Provider Tax ID | 333666999 | Alphanumeric 2-80 Characters |
| Subscriber Name | JANE DOE | Alphanumeric 1-25, 1-35 Characters |
| Subscriber ID | XXX123456789 | Alphanumeric 2-80 Characters |
| Patient Name | JOHN DOE | Alphanumeric 1-25, 1-35 Characters |
| Patient Street Address | 1234 SMALL LN | Alphanumeric 1-55 Characters |
| Patient City/State/ZIP | AUSTIN TX 12345 | Alphanumeric 2-30/2/Valid ZIP |
| Patient Date of Birth | 19810911 | CCYYMMDD |
| Patient Sex | M | F/M |

In an embodiment, the minimum level for the example above would be to validate that the data in the request is in the correct structural format. For example, the code for the payer name should be in the following format:

NM1*PR*2*PAYERX*****PI*123456~ with the payer name field containing 1-35 alphanumeric characters. The complete level would be to process the data in each field, such as "PAYER X".

In another embodiment, the minimum level would be to validate that the data in the request is in the correct structural format and also to process the data in the set of fields shown in the example, which are common to both the ANSI 270 request and the ANSI 271 response. The complete level would be to process the data in the fields not in the minimum level set, which are not shown in the above example and might amount to hundreds of lines of code.

Step 1020 in FIG. 4—In the first step with a minimum level and a complete level, processing the minimum and complete levels in parallel, when possible.

Figure 5:
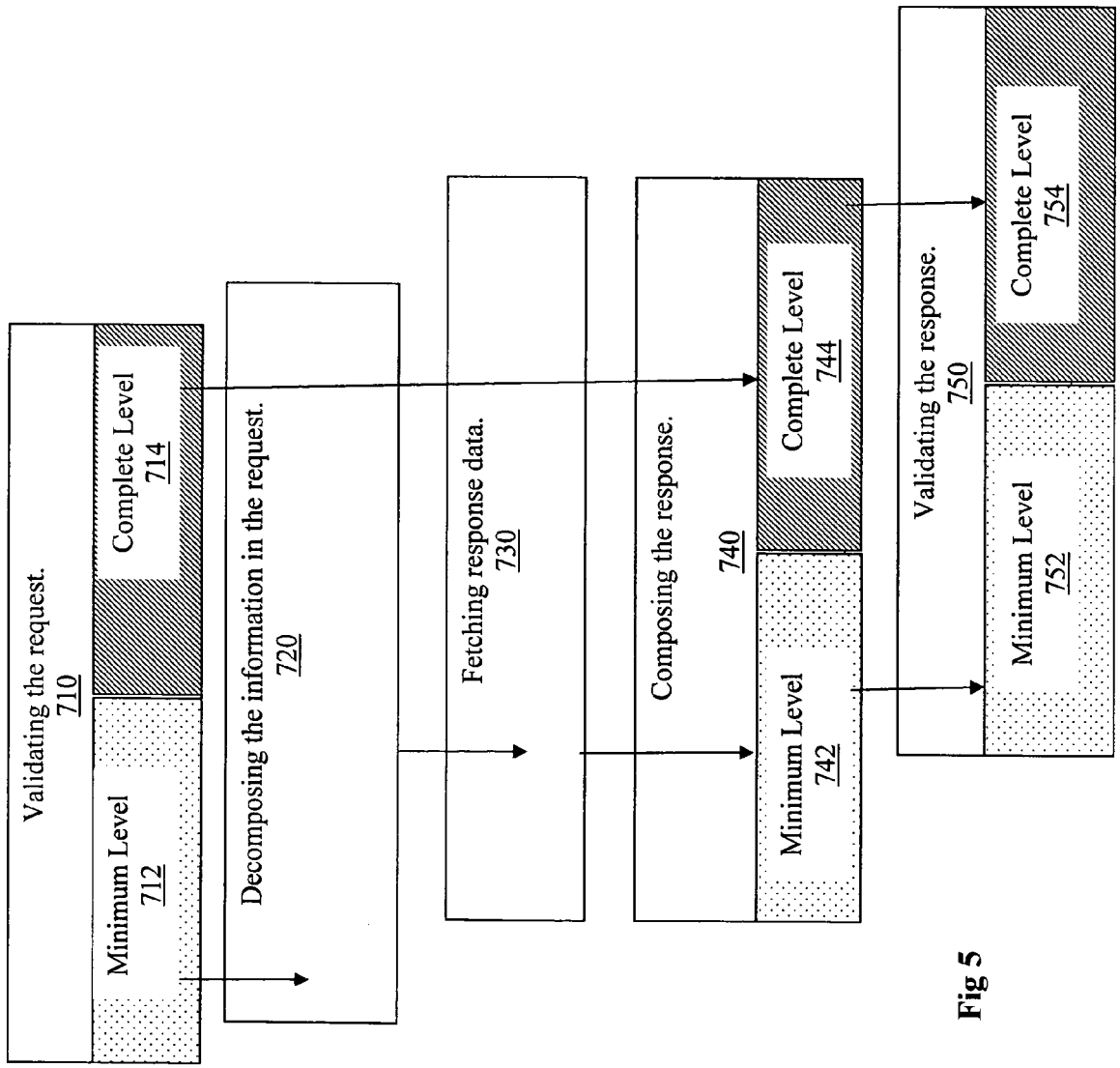
FIG. 5 is a flow chart that shows an example of the parallel processing employed by the parallel-processing response application.

The next step is to process the two levels in parallel. For example, FIG. 5 shows a scenario where the first step in composing a response, validating the request 710, can be divided into a minimum level 712 and a complete level 714. To follow the example of an ANSI 270 request and an ANSI 271 response from above, the minimum level 712 may comprise validating the structure of the code. The complete level 714 would then comprise processing the data in the fields within the code.

Figure 7:
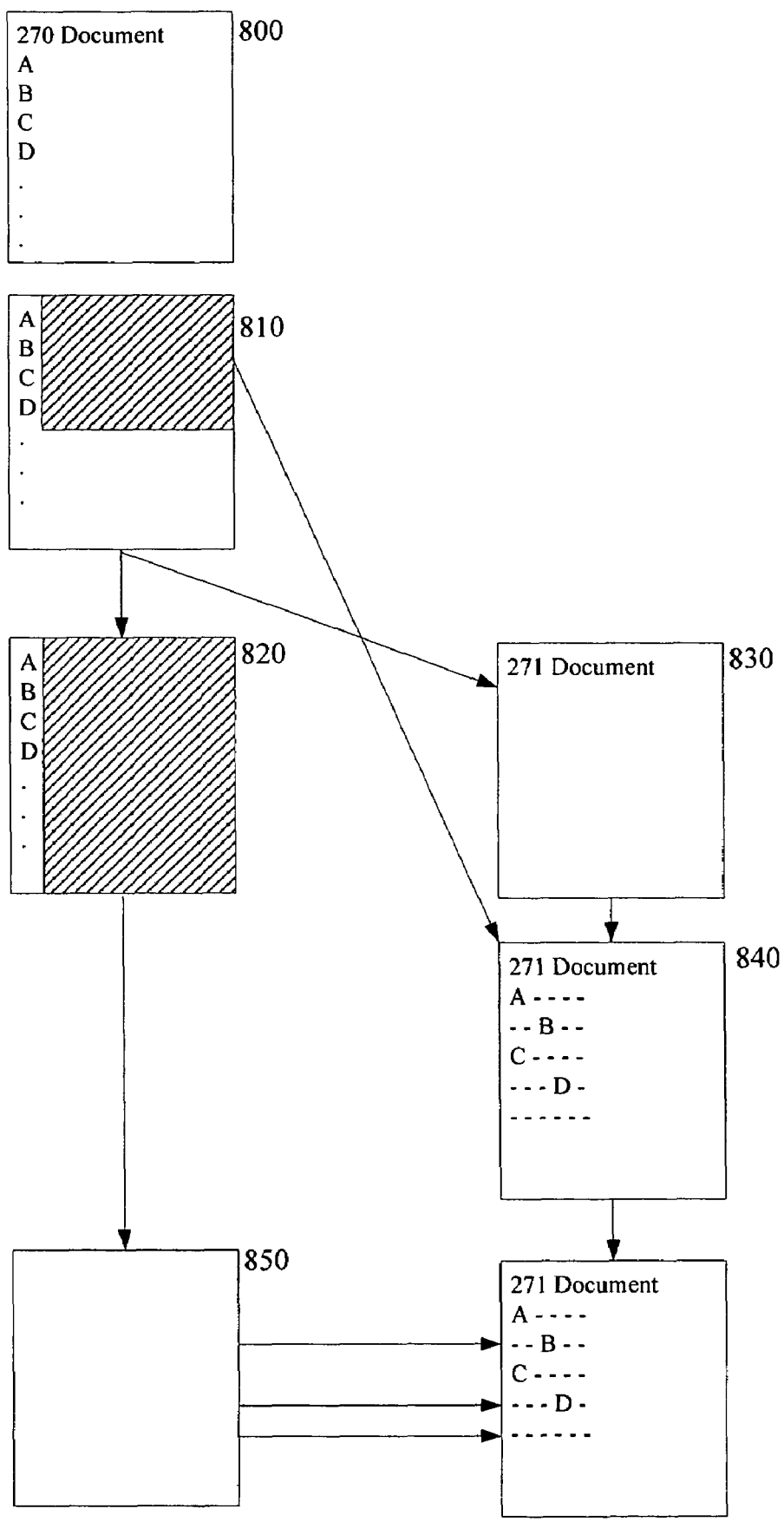
FIG. 7 is a schematic diagram illustrating using parallel processing to establish a structurally complete response with partial information.

FIG. 7 is a schematic illustrating the parallel processing to establish a structurally complete response with partial information. At step 800 an electronic request is received. In this case, the request is a 270 document.

At step 810 the validation of the request is completed to a minimum level. In this example, the validation includes data elements A, B, C, and D which are a subset of the data in the request. In other examples, the validation may be only of the structure of the request.

At step 820 the validation of the request is completed. In parallel with step 820, at step 830 the response structure is predetermined. In this example, the response is a 271 document. In other embodiments, the structure is a response template which is predetermined by personalization factors of the requesting party. The response template may be created upon receipt and partial validation of the request, or it may be recalled from memory or storage.

At step 840 the response document is prepopulated with data common to the request and the response. In this case, the data elements A, B, C, and D are common to the request and the response, but will typically not be in the same positions in the request and the response.

At step 850 the response document is filled in as subsequent processing determines additional data for the response.

In this example, the parallel processing permits the response structure to be determined and partially filled in while the validation and subsequent processing are being conducted. This parallel processing permits a shorter response time for the request.

Step 1030 in FIG. 4—Processing subsequent steps immediately after processing any minimum level in the preceding step and in parallel with any processing of the complete level of the preceding step.

FIG. 5 shows how the processing may proceed after Step 1020. After processing the minimum level 712 of validating the request 710, the parallel-processing response application 200, shown in FIG. 2, proceeds to the next step, decomposing the information in the request 720, shown in FIG. 5.

In parallel, processing the complete level 714 of validating the request 710 continues.

After decomposing the information in the request 720, fetching the response data 730 is accomplished.

After fetching the response data 730, processing begins on the minimum level 742 of composing the response 740, comprising creating the structure of the response.

After processing the complete level 714 of validating the request 710, processing begins on the complete level 744 of composing the response 740, comprising filling in the data of the response.

After processing the minimum level 742 of composing the response 740, processing begins on the minimum level 752 of validating the response 750, comprising validating the structure of the response.

After processing the complete level 744 of composing the response 740, processing begins on the complete level 754 of validating the response 750, comprising validating the data in the fields contained in the responses.

Because the above processing is accomplished in parallel, overall processing time can be decreased significantly. Although the decrease may only be measured in seconds for an individual transaction, saved seconds mount up over the hundreds of thousands of transactions that a business may require in an hour.

Computer System Overview

Figure 6:
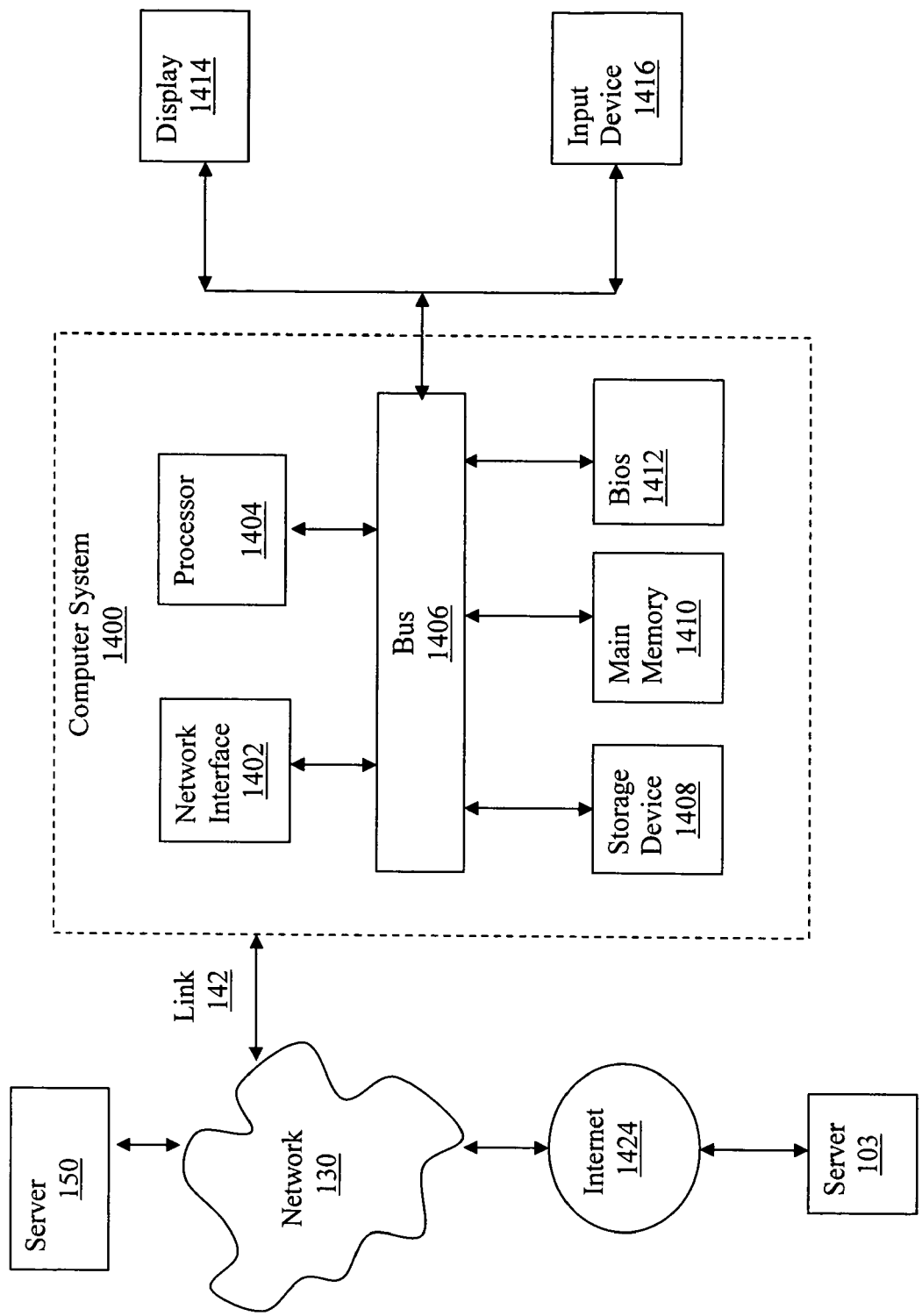
FIG. 6 is a block diagram that illustrates a typical computer system, representing a server on which embodiments of the present invention can be implemented.

FIG. 6 is a block diagram that illustrates an example of a typical computer system 1400, well known to those skilled in the art, representing a server on which embodiments of the present invention can be implemented. This computer system 1400, shown in FIG. 6, comprises a network interface 1402 that provides two-way communications through a wired or wireless link 147 to a wired or wireless communications network 130 that uses any applicable communications technology. For example, the network 130 can comprise a public telephone network, a wireless network, a local area network (LAN), and any known or not-yet-know applicable communications technologies, using correspondingly applicable links. The network 130 in turn provides communications with one or more host computers 150 and, through the Internet 1424, with one or more servers 103.

The network interface 1402 is attached to a bus 1406 or other means of communicating information. Also attached to the bus 1406 are the following:

a processor 1404 for processing information;

a storage device 1408, such as an optical disc, a magneto-optical disc, or a magnet disc, for storing information and instructions;

main memory 1410, which is a dynamic storage device such as a random access memory (RAM) that stores information and instructions to be carried out by processor 1404;

a bios 1412 or another form of static memory such as read only memory (ROM), for storing static information and instructions to be carried out by processor 1404;

a display 1414, such as a liquid crystal display (LCD) or cathode ray tube (CRT) for displaying information to user of the computer system 1400; and an input device 1416, with numeric and alphanumeric keys for communicating information and commands to processor 1404. In another embodiment a mouse or other input devices can also be used.

The computer system 1400 is used to implement the methods of the present invention in one embodiment. However, embodiments of the present invention are not limited to specific software and hardware configurations. Computer system 1400 can receive data from computer 150 and server 103 through a network 130 such as the Internet, and appropriate links 147, such as wired or wireless ones, and its network interface 1402. It can of course transmit data back to computers over the same routes.

Computer system 1400 carries out the methods of the present invention when its processor 1404 processes instructions contained in its main memory 1410. Another computer-readable medium, such as its storage device 1408, may read these instructions into main memory 1410 and may do so after receiving these instructions through network interface 1402. Processor 1404 further processes data according to instructions contained in its storage device 1408. Data is relayed to appropriate elements in computer system 1400 through its bus 1406. Instructions for computer system 1400 can also be given through its input device 1416 and display 1414.

"Computer-readable medium" refers to any medium that provides instructions to processor 1404, comprising volatile, non-volatile, and transmission media. Volatile media comprise dynamic memory, such as main memory 1410. Non-volatile media comprise magnetic, magneto-optical, and optical discs, such as storage device 1408. Transmission media comprise a wide range of wired and unwired transmission technology, comprising cables, wires, modems, fiber optics, acoustic waves, such as radio waves, for example, and light waves, such as infrared, for example. Typical examples of widely used computer-readable media are floppy discs, hard discs, magnetic tape, CD-ROMs, punch cards, RAM, EPROMs, FLASH-EPROMs, memory cards, chips, and cartridges, modem transmissions over telephone lines, and infrared waves. Multiple computer-readable media may be used, known and not yet known, can be used, individually and in combinations, in different embodiments of the present invention.

ALTERNATE EMBODIMENTS

It will be apparent to those skilled in the art that different embodiments of the present invention may employ a wide range of possible hardware and of software techniques. For example the communication between servers could take place through any number of links, including wired, wireless, infrared, or radio ones, and through other communication networks beside those cited, including any not yet in existence.

Also, the term computer is used here in its broadest sense to include personal computers, laptops, telephones with computer capabilities, personal data assistants (PDAs) and servers, and it should be recognized that it could include multiple servers, with storage and software functions divided among the servers. A wide array of operating systems, compatible e-mail services, Web browsers and other communications systems can be used to transmit messages among servers.

Furthermore, in the previous description the order of processes, their numbered sequences, and their labels are presented for clarity of illustration and not as limitations on the present invention.

What is claimed is:

1. A system for the automatic parallel processing of tasks involved in composing an electronic response to a structured electronic request comprising:

a first server, such that the first server can communicate with at least a second server to send and receive electronic messages; and a parallel-processing response application on the first server, such that the parallel-processing response application:

receives a structured electronic request from the second server;

performs validation of the structured electronic request to a first level of validation; and initiates subsequent processing of the structured electronic request in parallel with performing validation of the structured electronic request from the first level of validation to complete validation, the subsequent processing of the structured electronic request comprising predetermining a format of an electronic response document and selectively populating the electronic document with at least a portion of the data from the structured electronic request, wherein a completed electronic response document is communicated back to the second server.

2. A method of composing an electronic response to a structured electronic request comprising:

obtaining a structured electronic request associated with a requesting party that requires an electronic response, wherein the structured electronic request and the electronic response have at least one common field of information;

defining a process for validating the structured electronic request, the process for validating being segmented into at least validating the structured electronic request to a first level and validating the structured electronic request from the first level to a second level, wherein validating to the second level comprises complete validating of the structured electronic request;

composing an electronic response document by:

validating the structured electronic request at least to the first level; and initiating subsequent processing of the structured electronic request in parallel with completing a remainder of the process for validating the structured electronic request after validating the structured electronic request at least to the first level;

wherein the subsequent processing comprises at least predetermining a format of the electronic response document and selectively populating the electronic response document with at least one common field of information; and sending the electronic response document to the requesting party.

3. The method of claim 2 wherein:

validating the structured electronic request at least to the first level comprises validating a structure of the structured electronic request, and completing the remainder of the process for validating the structured electronic request comprises processing data in the structured electronic request.

4. The method of claim 3 wherein validating the structure of the structured electronic request comprises validating a required format of the structured electronic request and processing data from a specified set of fields in the structured electronic request.

5. The method of claim 2 wherein:
validating a structured electronic request at least to the first level comprises:
validating a structure of the structured electronic request, the structured electronic request comprising a first specified set of fields and a second set of fields; and
processing data from the first specified set of fields in the structured electronic request, and
initiating subsequent processing of the structured electronic request in parallel with completing the remainder of the process for validating the structured electronic request comprises processing data from the second set of fields of the structured electronic request.

6. The method of claim 2 wherein obtaining a structured electronic request comprises receiving an electronic data interchange from the requesting party.

7. The method of claim 6 wherein:
obtaining a structured electronic request comprises receiving a Health Insurance Portability and Accountability Act (HIPAA) request from the requesting party;
and sending the electronic response document to the requesting party comprises sending a HIPAA response to the requesting party.

8. The method of claim 6 wherein:
obtaining a structured electronic request comprises receiving an Association for Cooperative Operations Research and Development (ACORD) request from the requesting party; and
sending the electronic response document to the requesting party comprises sending an ACORD response to the requesting party.

9. The method of claim 2 wherein predetermining a format of the electronic response document comprises:
identifying the requesting party;
determining a preferred format of the electronic response document for the requesting party; and
preparing a response template for the electronic response document.

10. The method of claim 2, wherein predetermining a format of the electronic response document comprises identifying the requesting party and retrieving a response template from storage for the requesting party.

11. The method of claim 2 wherein selectively populating the electronic response document with at least one common field of information comprises identifying a portion of data in the structured electronic request which is common between the structured electronic request and the electronic response document and populating the electronic response document with each identified portion of data that is common between the structured electronic request and the electronic response document.

12. A method for the automatic parallel processing of tasks performed in the process of composing an electronic response to a structured electronic request comprising:
obtaining a structured electronic request from a first application on a first server;
defining a process for validating the structured electronic request, the process for validating being segmented into at least validating the structured electronic request to a first level and validating the structured electronic request from the first level to a second level, wherein validating to the second level comprises complete validating of the structured electronic request;
processing the structured electronic request with a parallel-processing response application to compose an electronic response document by:
validating the structured electronic request at least to the first level;
initiating subsequent processing of the structured electronic request in parallel with completing a remainder of the process for validating the structured electronic request after validating the structured electronic request at least to the first level;
wherein the subsequent processing comprises at least predetermining a format of the electronic response document and selectively populating the electronic response document with at least a portion of data extracted from the structured electronic request; and
sending the electronic response document to at least one requesting party.

13. The method of claim 12 wherein:
validating the structured electronic request at least to the first level comprises validating a structure of the structured electronic request; and
completing the remainder of the process for validating the structured electronic request comprises processing data in the structured electronic request.

14. The method of claim 13 wherein validating the structure of the structured electronic request comprises validating a required format of the structured electronic request and processing data from a specified set of fields in the structured electronic request.

15. The method of claim 13 wherein:
validating the structured electronic request at least to the first level further comprises:
validating the structure of the structured electronic request, wherein the structured electronic request comprises a first specified set of fields and a second set of fields; and
processing data from the first specified set of fields in the structured electronic request, and
initiating subsequent processing of the structured electronic request in parallel with completing the remainder of the process for validating the structured electronic request further comprises processing data from the second set of fields of the structured electronic request.

16. The method of claim 12 wherein obtaining a structured electronic request from a first application on a first server comprises receiving an electronic data interchange at a second server and providing the electronic data interchange to the parallel-processing response application.

17. The method of claim 16 wherein:
obtaining a structured electronic request from a first application on a first server comprises receiving a HIPAA request from the first application; and
sending the electronic response document to at least one requesting party comprises sending a HIPAA response to at least one requesting party.

18. The method of claim 16 wherein:
obtaining a structured electronic request from a first application on a first server comprises receiving an ACORD request from the first application; and sending the electronic response document to at least one requesting party comprises sending an ACORD response to at least one requesting party.

19. The method of claim 12 wherein predetermining a format of the electronic response document comprises:
   identifying at least one requesting party:
   determining a preferred format of the electronic response document for each requesting party; and
   preparing a response template for the electronic response document for each requesting party.

20. The method of claim 12 wherein selectively populating the electronic response document with at least a portion of the data extracted from the structured electronic request comprises identifying a portion of data in the structured electronic request which is common between the structured electronic request and the electronic response document and populating the electronic response document with at least a portion of the portion of data which is common between the structured electronic request and the electronic response document.

* * * * *